(12) United States Patent
Alzahrani et al.

(10) Patent No.: US 10,863,964 B1
(45) Date of Patent: Dec. 15, 2020

(54) INFRARED ALIGNMENT GUIDE FOR AN X-RAY MACHINE

(71) Applicant: KING SAUD UNIVERSITY, Riyadh (SA)

(72) Inventors: Ahmed Ibrahim Alzahrani, Riyadh (SA); Asma'a Abdurrahman Al-Ekrish, Riyadh (SA); Tariq Alshawi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/889,762

(22) Filed: Jun. 1, 2020

(51) Int. Cl.
*A61B 6/00* (2006.01)
*A61B 6/14* (2006.01)
*A61B 6/06* (2006.01)
*A61B 6/08* (2006.01)
*G06N 20/00* (2019.01)
*G06T 7/32* (2017.01)
*A61B 6/04* (2006.01)

(52) U.S. Cl.
CPC ............ *A61B 6/587* (2013.01); *A61B 6/0492* (2013.01); *A61B 6/06* (2013.01); *A61B 6/08* (2013.01); *A61B 6/145* (2013.01); *A61B 6/461* (2013.01); *G06N 20/00* (2019.01); *G06T 7/32* (2017.01); *A61B 2562/02* (2013.01); *G06T 2207/10116* (2013.01); *G06T 2207/30036* (2013.01)

(58) Field of Classification Search
CPC .. A61B 6/587; A61B 6/08; A61B 6/06; A61B 6/461; A61B 6/145; A61B 6/0492; A61B 2562/02; G06T 7/32; G06T 2207/30036; G06T 2207/10116; G06N 20/00

USPC ..................................... 378/38–40, 205, 206
See application file for complete search history.

(56) References Cited

U.S. PATENT DOCUMENTS

| 4,012,638 A | 3/1977 | Altschuler et al. |
| 7,090,395 B2 | 8/2006 | Glazer |
| 7,695,191 B1 * | 4/2010 | Buchanan ................. A61B 6/14 378/170 |
| 9,904,998 B2 | 2/2018 | Jockel et al. |
| 2013/0051528 A1 * | 2/2013 | Inglese ................... A61B 6/587 378/62 |
| 2019/0117183 A1 | 4/2019 | Lundt |

FOREIGN PATENT DOCUMENTS

| CN | 203736217 U | 7/2014 |
| CN | 108535285 A | 9/2018 |
| CN | 109124673 A | 1/2019 |

* cited by examiner

*Primary Examiner* — Courtney D Thomas
(74) *Attorney, Agent, or Firm* — Nath, Goldberg & Meyer; Richard C. Litman (57) ABSTRACT

The infrared alignment guide for an x-ray machine is used to align a target tooth and an x-ray sensor with transmitted x-rays, as well as aligning the transmitted x-rays with a most effective orientation for imaging the target tooth. The guide includes a body having an attached x-ray sensor holder. The x-ray sensor holder may be adjusted in relation to the body for imaging different teeth. The x-ray sensor holder emits infrared light towards the body, which is detected by an infrared camera on the front of the body. The image produced by the infrared camera, which shows the crowns of the teeth, is used to align the transmitted x-rays with the tooth and the x-ray sensor holder.

16 Claims, 6 Drawing Sheets

INFRARED ALIGNMENT GUIDE FOR AN X-RAY MACHINE

BACKGROUND

1. Field

The present disclosure relates to dental x-ray imaging, and in particular, to an infrared alignment guide for an x-ray machine that has an infrared alignment system for aligning a target tooth and x-ray sensor with transmitted x-rays, as well as aligning the transmitted x-rays with a most effective orientation for imaging the target tooth.

2. Description of the Related Art

In order to produce a diagnostic quality dental radiograph, there are three elements that need to be properly aligned: the x-ray beam, the tooth, and the x-ray sensor (which may be films, image plates, or solid-state digital sensors). A commonly used sensor technology in dental radiography is a solid-state sensor. Use of solid-state digital sensors in dental radiography is associated with difficulty in positioning the sensor correctly relative to the tooth and x-ray beam. Difficulty in confirming that the direction of the x-ray beam relative to the tooth and the sensor is correct prior to x-ray exposure and image formation often results in poor quality radiographs. This leads to many radiographs being of poor diagnostic quality, necessitating retaking the radiographs, up to 52% of the time for certain diagnostic tasks, resulting in increasing the radiation dosage to patients.

There have been previous attempts to help improve the relationship between the x-ray beam and x-ray sensors. However, such systems do not provide guidance for proper positioning of the x-rays and/or sensor relative to the tooth. In addition, many systems do not allow the optimum relationship of the x-ray beam, the tooth, and the x-ray sensor to be detected prior to exposing the patients to the x-rays.

Thus, an infrared alignment guide for an x-ray machine solving the aforementioned problems is desired.

SUMMARY

The infrared alignment guide for an x-ray machine is used to align a target tooth and an x-ray sensor with transmitted x-rays, as well as to align the transmitted x-rays with a most effective orientation for imaging the target tooth. The guide includes a tubular body, which may be slid over the cylindrical positioning indicating device (PID) of the x-ray machine. An attachment member extends out from the body to support an x-ray sensor holder for placement in a mouth of a patient. The position of the attachment member and the x-ray sensor holder may be adjusted for imaging different teeth and/or producing different types of images.

The x-ray sensor holder emits infrared light towards the body, which is detected by an infrared camera on a front of the body. The image produced by the infrared camera, which shows the crowns of the teeth, is used to align the transmitted x-rays with the tooth and the x-ray sensor holder.

A method of aligning an x-ray machine includes attaching the infrared alignment guide to the PID of the x-ray machine. An x-ray sensor is then attached to the sensor holder, and the guide is adjusted for imaging a desired tooth. The sensor holder is then inserted into the patient's mouth, and the infrared light source and camera are powered on. A display on an image processing unit, and/or a program in the image processing unit, is then used to adjust the position of the x-ray machine for optimal alignment of the transmitted x-rays, the target tooth, and the x-ray sensor.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The infrared alignment guide for an x-ray machine includes a tubular body, which may be slid over the cylindrical positioning indicating device (PID) of the x-ray machine. An attachment bar extends out from the body to support an x-ray sensor holder for placement in the mouth of a patient. The position of the attachment member and the x-ray sensor holder may be adjusted for different teeth and/or types of images. The x-ray sensor holder emits infrared light towards the tubular body, which is detected by an infrared camera on a front of the body. The image produced by the infrared camera, which shows the crowns of the teeth, is used to align the transmitted x-rays with the tooth and the x-ray sensor holder.

Figure 4:
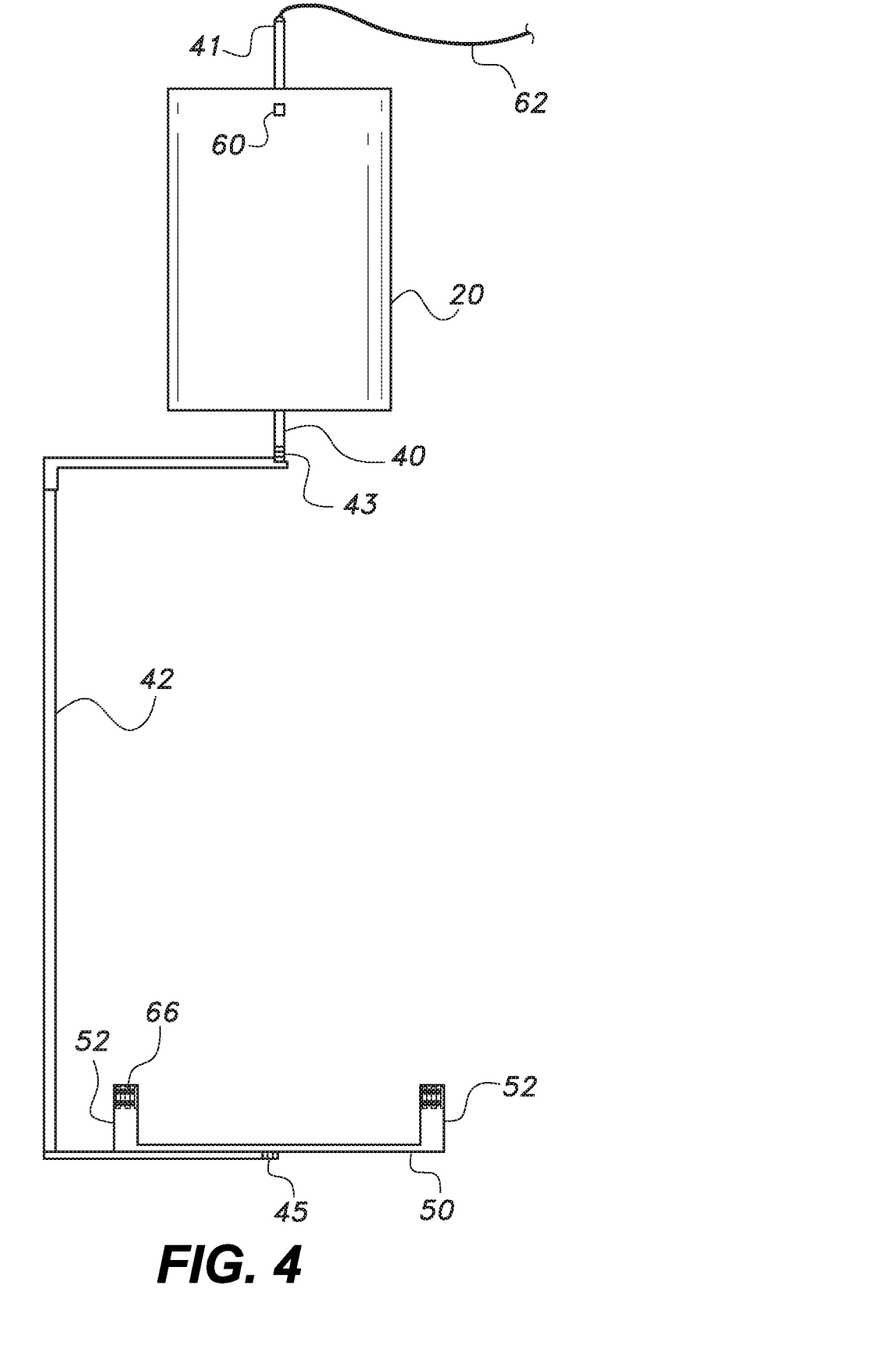
FIG. 4 is a top view of the alignment guide of FIG. 1.
Figure 5:
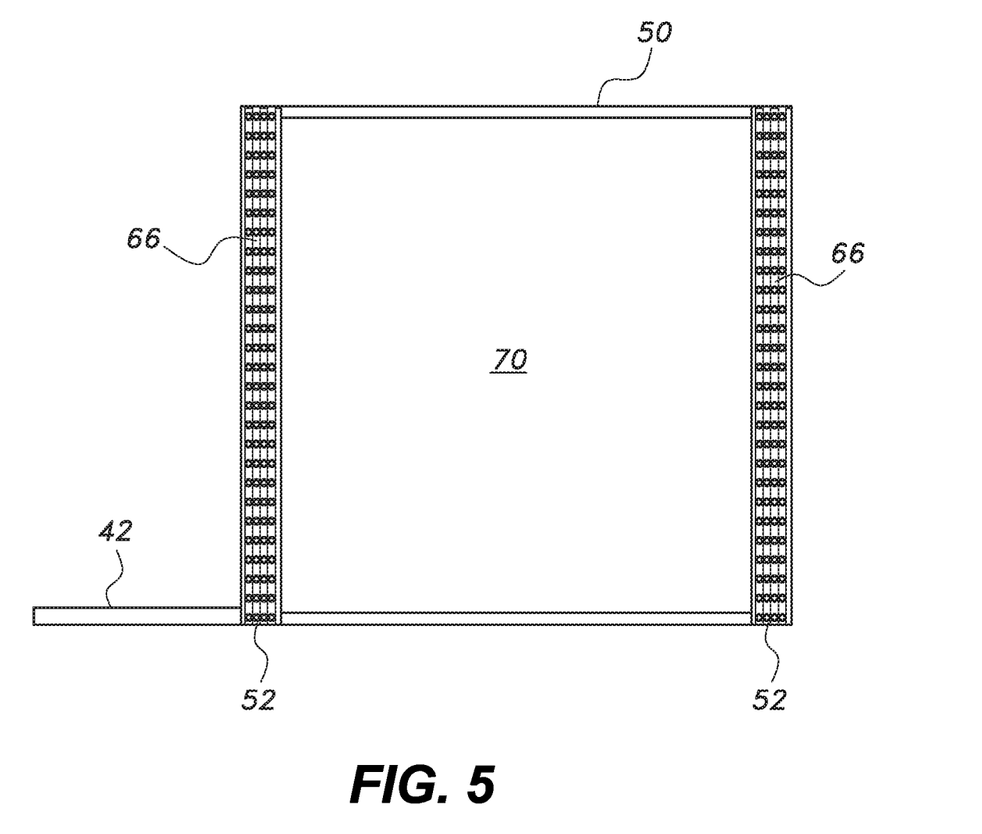
FIG. 5 is an elevational view of the x-ray sensor holder as seen from the front end of the body of the alignment guide of FIG. 1.
Figure 6:
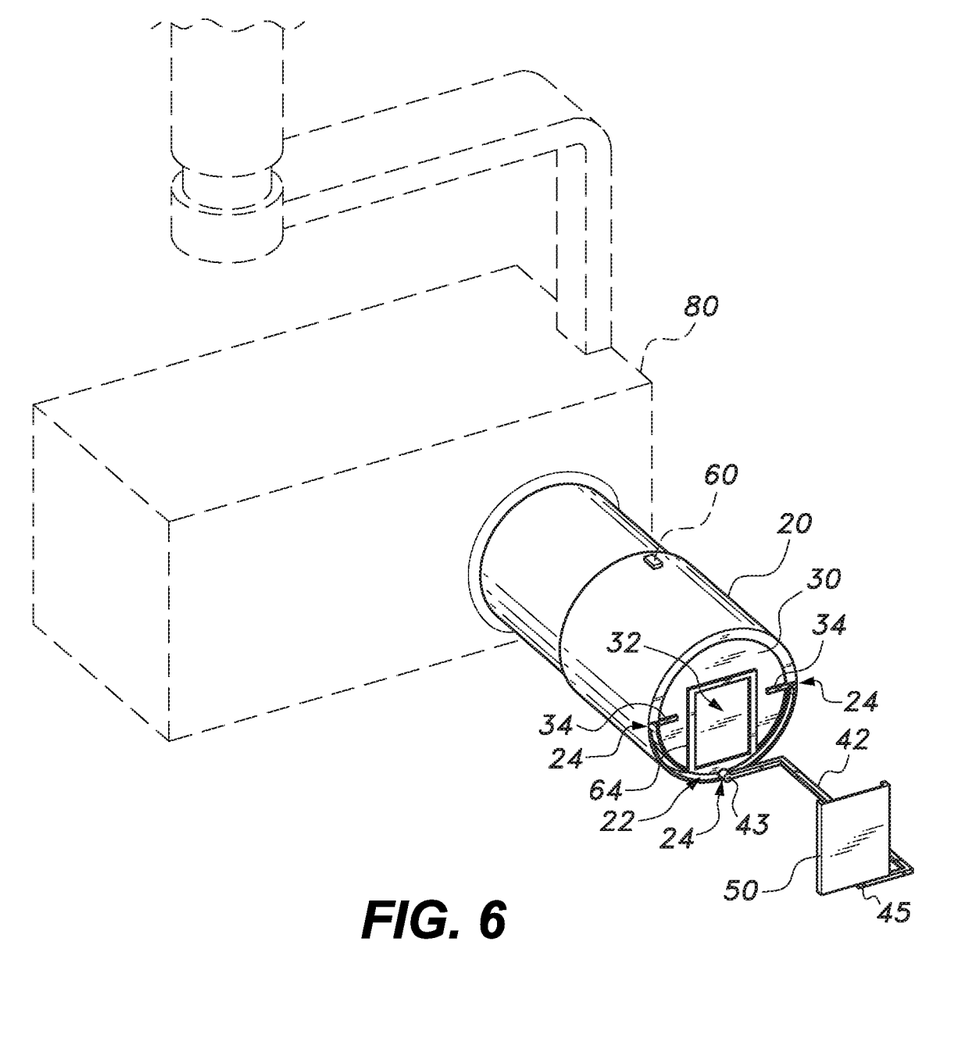
FIG. 6 is an environmental perspective view of the alignment guide of FIG. 1, shown attached to an x-ray machine.

FIGS. 1-6 show an embodiment of the infrared alignment guide 100 for an x-ray machine. The guide 100 includes a tubular body 20 having a collimator 30 at its front end. The length of the tubular body 20 may be determined based on the length of an X-ray machine's PID. For example, as shown in FIG. 6, the length of the tubular body 20 may be designed to extend along only one-half of the length of the PID. The collimator 30 includes an opening 32 to allow x-rays to pass through. The opening 32 may be dimensioned and configured to only pass x-rays that are directed at an associated x-ray sensor 70, thus preventing a patient from being exposed to unnecessary radiation. In some embodiments, the collimator opening 32 may be rectangular, in order to match a rectangular x-ray sensor 70. The collimator 30 may be made from a high density material, such as lead or other material known in the art that absorbs almost all x-ray radiation. An infrared camera 64 may be attached to the front surface of the collimator 30. The camera 64 may be, for example, a Melexis MLX90640, which includes an array of infrared sensors.

Figure 1:
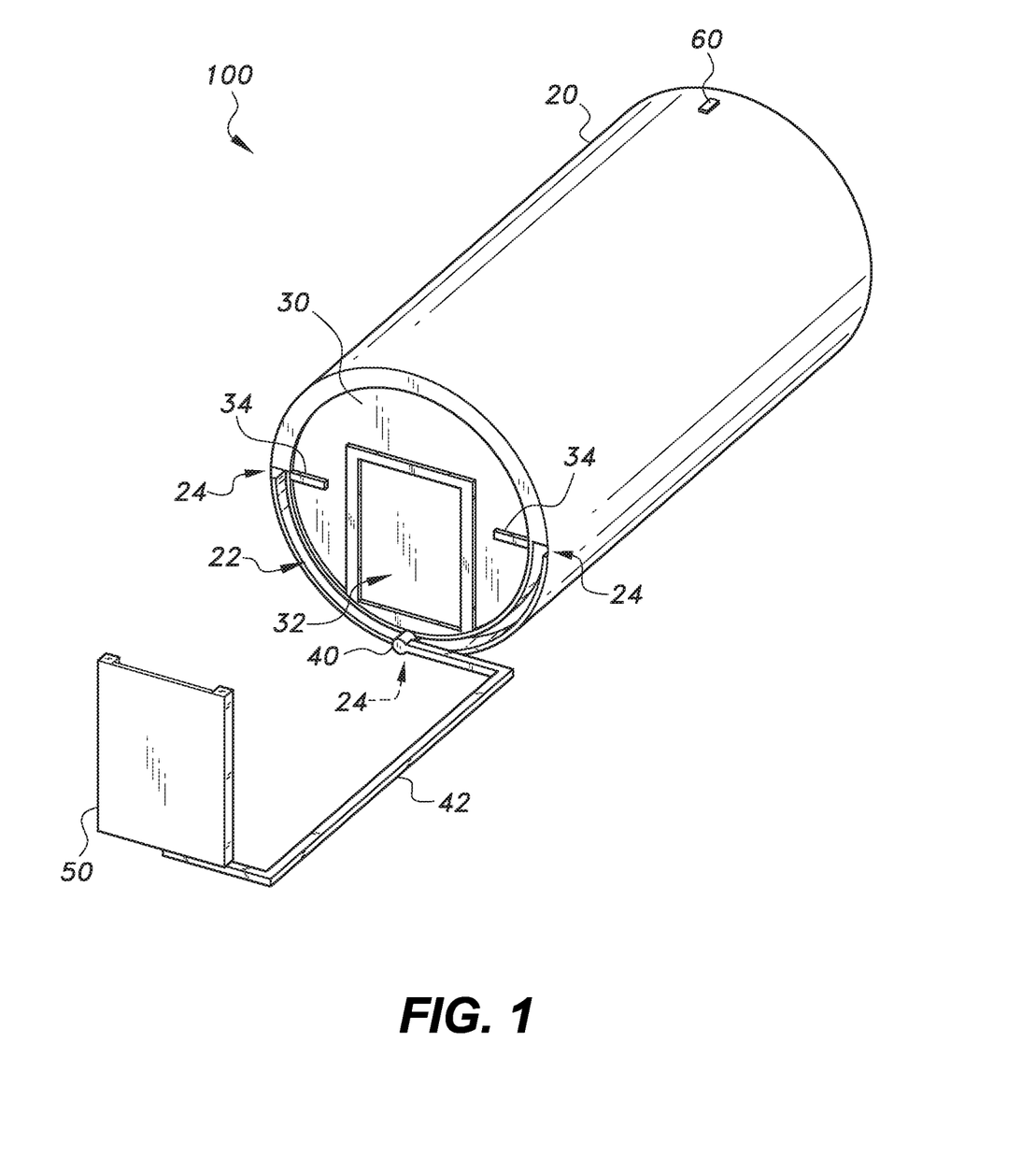
FIG. 1 is a perspective view of an infrared alignment guide for an x-ray machine.
Figure 2:
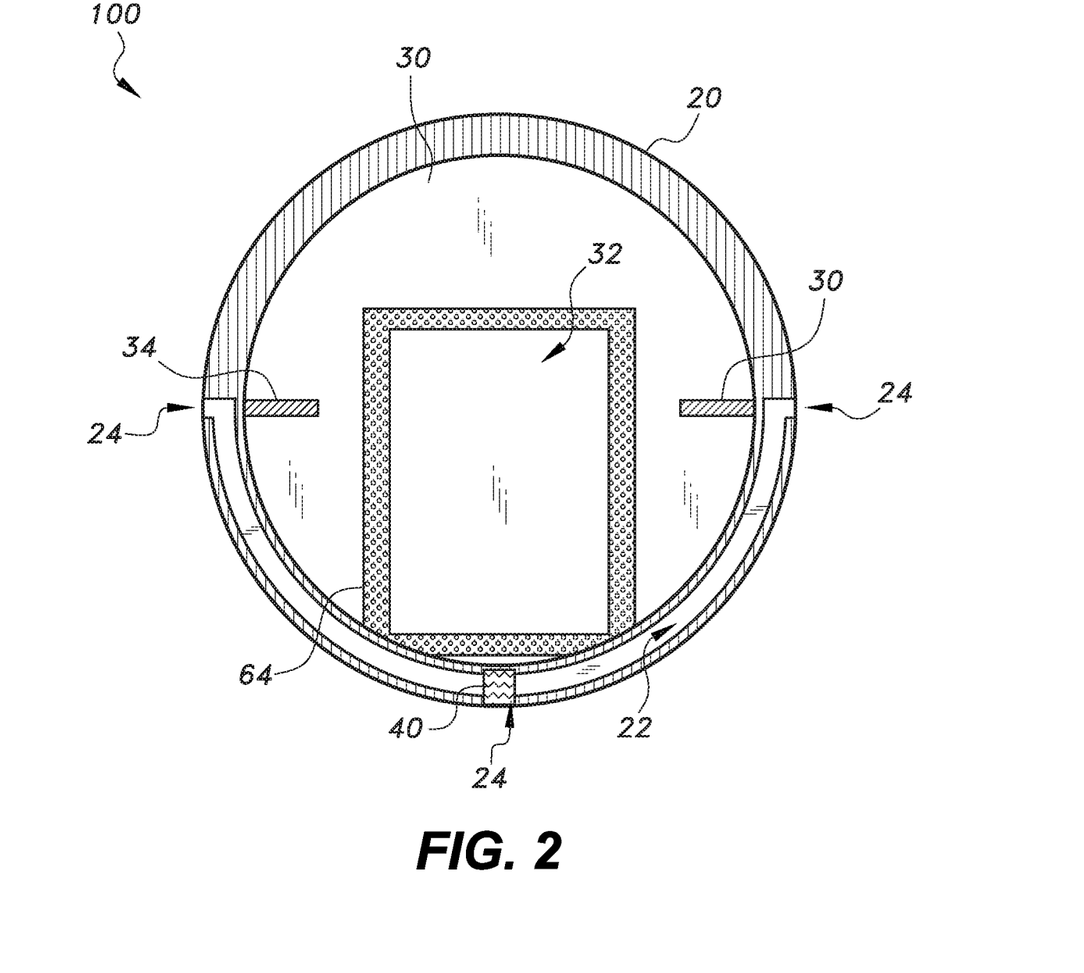
FIG. 2 is a front view of the alignment guide of FIG. 1, shown with the attachment member and x-ray sensor holder removed.
Figure 3:
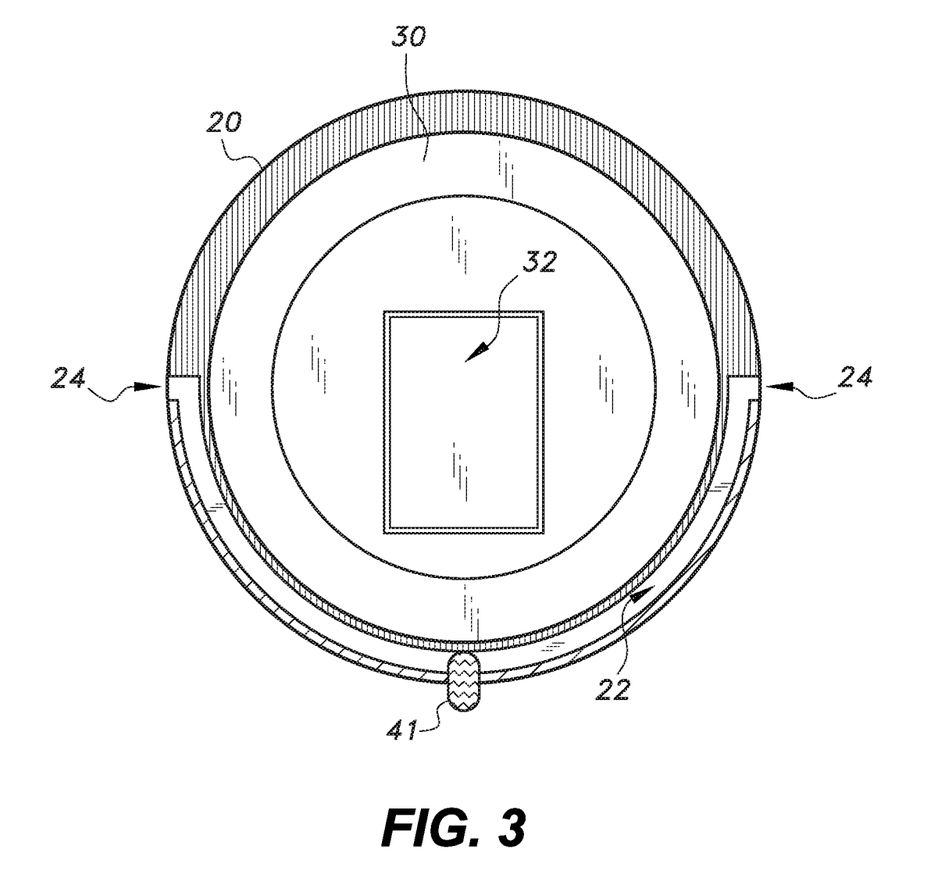
FIG. 3 is a rear view of the alignment guide of FIG. 1.

The wall of the tubular body 20 has a thickness in which a channel 22 is defined that extends from the front of the tubular body 20 to the back. The channel 22 may extend circumferentially around 180° of the tubular body 20. A support bar 40 may be positioned within the channel 22, the bar 40 having a first end extending out from a front of the channel 22 and an opposite second end extending out from a back of the channel 22. The support bar 40 may be moved along the circumferential length of the 180° channel 22, as well as axially in and out of the channel 22; hence, the body of the support bar 40 is dimensioned in section for slidable movement in the channel 22. The channel 22 may define multiple slots 24 extending from the front to the back of the channel 22, spread apart along a circumference of the body 20. For example, as best seen in FIGS. 2-3, a slot 24 may be formed at each end of the channel 22, and also in the middle of the channel 22. The slots 24 may be designed to tightly accept a portion of the support bar 40, e.g. the head of the support bar 40, for locking the support bar 40 at the location of a slot 24 and at a set or predetermined angular orientation. Accordingly, the cross-sectional shape of the slots 24 may be dimensioned and configured to match the cross-sectional shape of the head of the support bar 40.

An attachment member 42 may be pivotally attached to a front end of the support bar 40 by an attachment hinge 43, best shown in FIG. 4. The attachment hinge 43 may by a single plane hinge operating in a plane perpendicular to a longitudinal axis of the support bar 40. The attachment member 42 may be formed to define two opposing right angle bends to form a substantially U-shaped member 42. In some embodiments, each end segment of the attachment member 42 may have a length of 1.5 inches, resulting in the central segment being offset 1.5 inches from the support bar 40.

An x-ray sensor holder 50 may be pivotally attached to the end of the attachment member 42 opposite the support bar 40. The holder 50 may be pivotally connected to the attachment member 42 by a sensor hinge 45, which operates in a plane parallel to the attachment hinge 43. The sensor holder 50 may define two side walls 52 extending out from a back wall. The side walls 52 of the sensor holder 50 may be adjusted laterally inwards and outwards to accept and secure x-ray sensors 70 of size 0, 1, and 2. A surface of the holder 50 facing the body 20 may include a source 66 of infrared light, such as infrared light emitting diodes (IRLEDS).

A button 60 to power on and power off the infrared camera 64 and light source 66 may be provided on the body 20 for operation by an operator aligning the attached x-ray machine 80. The support bar 40 and attachment member 42 may be hollow for accepting a power cord 62 that runs from a rear end of the support bar 40 to the infrared light source 66 on the holder 50. In some embodiments, the power cord 62 may branch to connect with the power button 60 and camera 64. Accordingly, the light source 66, camera 64, and power button 60 may be in electrical communication through the power cord 62. Power may be provided by an external power source, to which the power cord is connected. In some embodiments, the external power source may be connected via a power and data connection, such as a USB port. Alternatively, a power source, such as a battery provided in or on the tubular body 20, may be used to power the camera 64 and light source 66.

The camera 64 may output the captured image to an image processing unit, such as a personal computer, to display the real-time image for viewing by an operator. The data may be transmitted to the image processing unit via a physical cord, such as a data line through the power cord, or a wireless data connection. The image processing may include noise reduction, size modification, color segmentation, and compensation of intensity variance. A screen on the image processing unit may display the processed image.

FIG. 2 shows the front of an embodiment of the tubular body 20, collimator 30, and inserted support bar 40. The body 20 may include a tubular outer wall defining a circumferential channel 22 extending around 180° of the wall. The support bar 40 can reside within the channel 22 and may be moved circumferentially along the wall through the channel 22 to the multiple locking slots 24. The collimator 30 covers the front opening of the tubular body 20. An opening 32 is provided in the collimator 30 to allow only the X-rays directed at the x-ray sensor 70 to pass. Accordingly, the opening 32 may be dimensioned and configured based on the size and shape of the x-ray sensor 70 connected to the sensor holder 50. The infrared camera 64 may extend fully or partially around a perimeter of the opening 32. The collimator 30 may be rotatable relative to the body 20, allowing it to be aligned with the sensor support 50 as the support bar 40 is moved through the circumferential groove 22. Two tabs 34 for rotating the collimator 30 with respect to the tubular body 20 may be attached to the collimator 30.

FIG. 3 shows the tubular body 20, collimator 30, and inserted support bar 40 from the rear. As seen in FIG. 3, the circumferential groove 22 and support bar 40 extend through the length of the body 20. The support bar 40 may protrude out from the rear end of the body 20 and provide a tab 41 for an operator to adjust the position of the support bar 40. In some embodiments, the support bar 40 may be longer than the tubular body 20 to allow the distance between the sensor holder 50 and the tubular body 20 to be adjusted by moving the support bar 40 along its longitudinal axis through the channel 22.

FIG. 4 is a top view of the guide 100, showing the hinged connections between the support bar 40, attachment member 42, and the sensor holder 50. The support bar 40 may attach to the attachment member 42 by the attachment hinge 43, which pivots in a plane perpendicular to the longitudinal axis of the support bar 40. The sensor holder 50 may be connected to the attachment member 42 by a sensor hinge 45, which may operate in a plane parallel to the operating plane of the attachment hinge 43.

The sensor holder 50 may include two vertical walls 52 extending out from opposing sides of the back wall. A light source 66 may be connected to the surface of the walls 52 facing the collimator opening 32 and the infrared camera 64 of the guide 100. In use, the x-ray sensor 70 is held between the walls 52, which may be adjusted inwards and outwards to accept different sizes of x-ray sensors 70. Accordingly, a location of the x-ray sensor's perimeter can be determined based on the location of the light source 66.

FIG. 5 shows a front view of the sensor holder 50. The light source 66, which may include one or more IRLEDs, may be dispersed along the vertical walls 52 of the holder 50. As previously discussed, the light source 66 is oriented to direct light at the camera 64 on the collimator 30 of the guide 100. The light source 66 may be powered through an electrical cord 62 extending through the support bar 40 and attachment member 42. In some embodiments, the light source 66 may only emit light in the near-infrared range, which includes wavelengths of 750 nm to 2500 nm. Accordingly, the infrared camera 64 may be tuned to only capture light waves in the near-infrared range. In some embodiments, one or more Boston Electronics EP-4317 IRLEDs may be used as the light source 66. In some embodiments, the light source 66 may produce any or all infrared wavelengths and the camera 64 may be tuned accordingly.

A method of using the guide 100 may include first sliding the adapter 100 over the PID of an x-ray machine 80. The user may then adjust the sensor holder 50 to adequately secure a desired x-ray sensor 70, which may be between sensor size 0 and sensor size 2. The opening 32 in the collimator 30 may also be adjusted to match the size of the x-ray sensor 70. The guide 100 may then be positioned based on the target teeth and the type of radiograph.

The following will discuss adjusting the guide 100 for periapical radiographs. If the upper left teeth are being imaged, the adapter 100 will be configured as seen in FIG. 6. To image the lower right teeth, the body 20 is rotated 180° around the PID relative to the position in FIG. 6. To image the upper right teeth, the body 20 is oriented as seen in FIG. 6, the attachment hinge 43 is rotated 180°, and the sensor hinge 45 is rotated 180° relative to the position in FIG. 6. To image the lower left teeth, the body 20 is rotated around the PID 180°, the attachment hinge 43 is rotated 180°, and the sensor hinge 45 is rotated 180°, all relative to the position shown in FIG. 6.

The following will discuss adjusting the guide 100 for bitewing radiographs. To image teeth on the left side of the mouth, the collimator 30 is rotated 90° counterclockwise, the support bar 40 is moved 90° counterclockwise along the channel 22, and the sensor hinge 45 is rotated 90° counterclockwise, all relative to the position shown in FIG. 6. To image teeth on the right side of a patient's mouth, the tubular body 20 is rotated 180°, the sensor hinge 45 is rotated 90° counterclockwise, the collimator 30 is rotated 90° counterclockwise, and the support bar 40 is moved 90° counterclockwise, all relative to the position shown in FIG. 6.

Once the guide 100 is configured for the intended image, based on the above discussion, and the sensor holder 50 with attached x-ray sensor 70 is placed in the patient's mouth, the camera 64 and light source 66 are powered on. The image obtained by the camera 64 will include the location of the light source 66, indicating the location of the x-ray sensor 70, and an outline of the teeth positioned in front of the x-ray sensor 70. The data from the camera 64 may then be sent to an image processing unit, which may display the image in real time. In some embodiments, the imaging processing unit may be a personal computing device, such as a desktop computer, laptop computer, or a tablet computer. Image processing may include noise reduction, size modification, color segmentation, and compensation of intensity variance.

To accurately align the transmitted x-rays and the x-ray sensor 70 with the target tooth or teeth, the x-ray machine 80, and therefore the attached guide 100, are adjusted until the target teeth or tooth are aligned between the collimator opening 32 (defining the path of the transmitted x-rays) and the x-ray sensor 70. Once the collimator opening 32, target teeth or tooth, and the x-ray sensor 70 are aligned, the operator may adjust the vertical and horizontal angulation of the x-ray machine's PID until the image produced by the image processing unit shows the appropriate projection geometry. For anterior teeth, the vertical angulation of the PID is adjusted so that there is no elongation of the crowns, and the horizontal angulation is adjusted until there is minimal overlap of the interproximal surfaces of adjacent teeth. For posterior teeth, the vertical angulation of the PID is adjusted so that there is maximum alignment of the buccal and lingual cusps, and the horizontal angulation is adjusted until there is minimal overlap of the interproximal surfaces of adjacent teeth. Once the PID is appropriately positioned, the operator will take the x-ray.

In some embodiments, determination of the correct horizontal and vertical angulation of the PID may be achieved using artificial intelligence. Specifically, the imaging processing unit may be programmed using machine learning to identify the parameters of optimum position, as stated above, based on the output of the camera. When the optimum position is achieved in each plane, the operator may be notified. This may be achieved by an alignment detector, which may produce an audible sound if the captured image indicates correct alignment or not. The alignment detector works by comparing the input (test) image with a dictionary of images taken at correct alignment. If there is a clear match, the algorithm declares correct alignment. Otherwise, it will direct the user to adjust the PID to reach better alignment.

To facilitate efficient computation and fast processing, the comparison procedure will be performed according to a machine learning algorithm known as nearest neighbor algorithm. A dictionary of correctly aligned images may be obtained through clinical trials, where researchers take x-ray images from multiple angles and consult a dentist on the most correct image alignment. Afterwards, the dictionary will be filled with images belonging to two classes: correctly aligned and misaligned. Using the collected dataset, the nearest neighbor algorithm is used to build a matching comparator that classifies a test image to be either correctly aligned or misaligned. For the learning algorithm parameters, a Euclidean distance of k=7 may be used.

It is to be understood that the infrared alignment guide for an x-ray machine is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. An infrared alignment guide for an x-ray machine, comprising:
    an elongated tubular body having a front end and a back end and defining a circumference, the body having an outer wall having a thickness in which a channel is defined, the channel having a length extending axially from the front end of the body to the back end of the body, the channel extending laterally around at least a portion of the circumference of the tubular body, the tubular body being adapted for mounting on the x-ray machine;
    a collimator positioned within the tubular body at the front end of the body;
    a support bar extending through the channel, the support bar having a front end and a back end;
    an attachment member having a front end and a back end;
    an attachment hinge, the back end of the attachment member being pivotally attached to the front end of the support bar by the attachment hinge;
    an x-ray sensor holder adapted for holding an x-ray sensor;
    a sensor hinge pivotally attaching the x-ray sensor holder to the front end of the attachment member;
    an infrared light source mounted on the sensor holder, the infrared light source being configured to emit infrared light towards the collimator; and
    an infrared light sensor attached to the collimator, the infrared light sensor being configured to sense infrared light emitted from the infrared light source.

2. The infrared alignment guide of claim 1, wherein the outer wall of the tubular body defines a plurality of slots connecting with the channel, the slots being spaced apart and extending along the entire length of the channel.

3. The infrared alignment guide of claim 2, wherein the slots are dimensioned and configured to receive the support bar for securing the support bar at the locations of the slots.

4. The infrared alignment guide of claim 2, wherein the plurality of slots consists of a first slot at a first lateral end of the channel, a second slot at an opposing second lateral end of the channel, and a third slot midway between the first and second slots.

5. The infrared alignment guide of claim 1, wherein the channel extends circumferentially around 180° of the wall.

6. The infrared alignment guide of claim 1, wherein said infrared sensor is configured for transmitting infrared images to an image processor for display to a user of the guide.

7. The infrared alignment guide of claim 1, wherein the attachment hinge and the sensor hinge operate in planes perpendicular to a longitudinal axis of the support bar.

8. The infrared alignment guide of claim 1, wherein the attachment member includes two opposing bends to form a substantially U-shaped member.

9. The infrared alignment guide of claim 1, wherein the collimator is rotatable with respect to the tubular body.

10. The infrared alignment guide of claim 1, wherein the support bar has a length greater than the length of the channel to provide for forward and backward adjustability.

11. The infrared alignment guide of claim 1, wherein the x-ray sensor holder is adjustable for securing x-ray sensors of different sizes.

12. An infrared alignment guide for an x-ray machine, comprising:
 a body configured for attachment to a position indicator device of the x-ray machine;
 an x-ray sensor holder adjustably connected to the body, the x-ray sensor holder being adapted for positioning in a patient's mouth for periapical and bitewing dental x-rays of the patient's upper and lower teeth on either side of the mouth;
 an infrared light source mounted on the sensor holder, the infrared light source being configured to emit infrared light in a direction towards the body of the guide; and
 an infrared light sensor mounted on the body, the infrared light sensor being configured to sense infrared light emitted by the infrared light source, the infrared light sensor being adapted for connection to a device for displaying infrared images to guide positioning of the x-ray machine.

13. A method of aligning an x-ray machine with an x-ray sensor for imaging teeth in a patient's mouth using an infrared alignment guide attached to the x-ray machine, comprising the steps of:
 inserting an x-ray sensor holder of the infrared guided alignment detector into a patient's mouth;
 emitting infrared light from the x-ray sensor holder and detecting the emitted infrared light using an infrared light sensor adjacent the x-ray machine;
 creating an image from infrared light detected by the infrared light sensor;
 adjusting position of the x-ray machine based on the image to improve alignment for x-ray imaging of the patient's teeth;
 providing an alarm indicating alignment is proper; and
 taking an x-ray when proper alignment is achieved.

14. The method of aligning an x-ray machine according to claim 13, wherein the step of adjusting the position of the x-ray machine includes the steps of:
 adjusting the position to center the patient's teeth on an x-ray sensor attached to the x-ray sensor holder; and
 adjusting the position of the x-ray machine to provide at least one of minimal elongation of the teeth's crowns, minimal overlap between the teeth, and maximal alignment of the buccal and lingual cusps.

15. The method of aligning an x-ray machine of claim 13, further comprising the step of using machine learning to determine when alignment is proper.

16. The method of aligning an x-ray machine of claim 15, wherein a nearest neighbor algorithm is used to determine if alignment is correct by comparing the created images with properly aligned and improperly aligned images.

* * * * *